United States Patent
Pierrès et al.

(10) Patent No.: US 8,318,712 B2
(45) Date of Patent: Nov. 27, 2012

(54) CONCENTRATED LIQUID THYROID HORMONE COMPOSITION

(75) Inventors: Cécile Pierrès, Nantes (FR); Atimad Gaugain-Hamidi, La Ferriére de Flée (FR)

(73) Assignee: Intervet International B.V., Boxmeer (NL)

( * ) Notice: Subject to any disclaimer, the term of this patent is extended or adjusted under 35 U.S.C. 154(b) by 893 days.

(21) Appl. No.: 12/160,292

(22) PCT Filed: Jan. 5, 2007

(86) PCT No.: PCT/EP2007/050107
§ 371 (c)(1),
(2), (4) Date: Mar. 12, 2009

(87) PCT Pub. No.: WO2007/077252
PCT Pub. Date: Jul. 12, 2007

(65) Prior Publication Data
US 2009/0270507 A1 Oct. 29, 2009

Related U.S. Application Data

(60) Provisional application No. 60/756,777, filed on Jan. 6, 2006.

(30) Foreign Application Priority Data

Jan. 6, 2006 (EP) .................................... 06100133

(51) Int. Cl.
*A61K 31/33* (2006.01)

(52) U.S. Cl. ........................................................ 514/183
(58) Field of Classification Search .................... 514/183
See application file for complete search history.

(56) References Cited

U.S. PATENT DOCUMENTS

| 4,983,586 A | 1/1991 | Bodor |
| 5,856,359 A | 1/1999 | Fischer et al. |
| 5,955,105 A | 9/1999 | Mitra et al. |
| 6,407,079 B1 | 6/2002 | Müller et al. |
| 2005/0186267 A1* | 8/2005 | Thompson et al. ........... 424/451 |

FOREIGN PATENT DOCUMENTS

| EP | 0463653 | 1/1992 |
| WO | 9520955 A1 | 8/1995 |
| WO | 9719703 A2 | 6/1997 |
| WO | WO 2005/004849 | 1/2005 |

OTHER PUBLICATIONS

T. Vanhaecke, et al. Biochemical Pharmacology 61:1073-1078 (2001).

* cited by examiner

*Primary Examiner* — Brandon Fetterolf
*Assistant Examiner* — Christopher R Stone
(74) *Attorney, Agent, or Firm* — TraskBritt

(57) ABSTRACT

This invention is directed generally to a liquid pharmaceutical composition comprising at least one thyroid hormone (particularly a composition further comprising at least one cyclodextrin compound), a process for making such a composition, and a method of using such a composition to treat a condition associated with impaired thyroid hormone function.

7 Claims, No Drawings

CONCENTRATED LIQUID THYROID HORMONE COMPOSITION

CROSS-REFERENCE TO RELATED PATENT APPLICATIONS

This patent claims priority under 35 U.S.C. §371 as a national phase of International Patent Application No. PCT/EP2007/050107 (filed Jan. 5, 2007; and published on Jul. 12, 2007 as International Publication No. WO 2007/077252), which, in turn, claims priority to U.S. Provisional Patent Application Ser. No. 60/756,777 (filed Jan. 6, 2006) and European Patent Application No. 06100133.5 (filed Jan. 6, 2006). The entire texts of the above-referenced patent applications are incorporated by reference into this patent.

FIELD OF THE INVENTION

This invention is directed generally to liquid pharmaceutical compositions comprising at least one thyroid hormone (particularly compositions further comprising at least one cyclodextrin compound), processes for making such compositions, and methods of using such compositions to treat conditions associated with impaired thyroid hormone function.

BACKGROUND OF THE INVENTION

Thyroid hormones are known to be useful in treating conditions associated with impaired thyroid hormone function. Impaired thyroid activity may, for example, occur spontaneously or be the result of surgical removal of the thyroid gland, thyroiditis, or decreased function secondary to pituitary degeneration resulting in hypothyroidism. Conditions secondary to the hypothyroidism include myxedema, cretinism, and obesity.

Thyroid hormones are generally unstable and insufficiently soluble in water for use in many conventional liquid compositions. Consequently, various solid dosage forms (e.g., tablets) have been used for administering such agents. Liquid dosage forms (particularly aqueous solutions), however, are often more convenient to administer (particularly to, for example, companion animals) compared to tablets and other solid dosage forms.

Thyroid hormones include, for example, levothyroxine. Levothyroxine is an iodinated amino acid of the thyroid gland that exerts a stimulating effect on metabolism. Kendall, *J. Am. Med. Assoc.*, 64, p. 2042 (1915). Levothyroxine is also known as L-thyroxine; L-T4; 0-(4-hydroxy-3,5-diiodophenyl)-3,5-diiodotyrosine; and L-3,5,3',5'-tetraiodothyronine. It is commercially available under various trade names, including Synthroid, Levothroid, Levoxyl, Unithroid, and Soloxine.

When used to treat a thyroid disorder, levothyroxine is often administered in the form of a sodium salt:

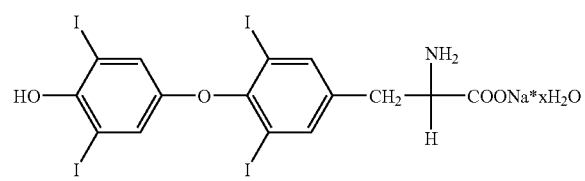

Such salts include, for example, levothyroxine sodium pentahydrate (CAS number: 6106-07-06) and levothyroxine sodium hydrate (CAS number: 25416-65-3). Levothyroxine sodium has conventionally been used in tablet form having a unit dose of about 0.1 mg per tablet.

International Patent Application Publication No. WO 95/20955 discusses liquid compositions comprising a thyroid hormone, including levothyroxine sodium. Those compositions reportedly contain from 40% to 96% ethanol (by volume) and from 4% to 50% water (by volume), and have a pH of from 9 to 12.

Various cyclodextrins have been reported to improve the solubility of sparingly-water-soluble compounds. For example, U.S. Pat. No. 6,407,079 discusses pharmaceutical compositions comprising inclusion compounds of sparingly-water-soluble or water-instable drugs with β-cyclodextrin ethers or esters. And U.S. Pat. No. 4,983,586 discusses the use of a composition comprising from 20% to 50% hydroxypropyl-β-cyclodextrin in a method for decreasing precipitation of a lipophilic or water-labile drug near the injection site and/or organs following parenteral administration.

U.S. Pat. No. 5,955,105 discusses levothyroxine compositions comprising a β-cyclodextrin. Those compositions, however, are characterized as being solid compositions, i.e., less than 4.5% (by weight) water.

International Patent Application Publication No. WO 97/19703 discusses oral, parenteral, and transdermal pharmaceutical compositions comprising levothyroxine sodium and an α-cyclodextrin, β-cyclodextrin, or γ-cyclodextrin. WO 97/19703 reports that γ-cyclodextrin provided the greatest improvement in the aqueous solubility for L-thyroxine sodium of the cylcodextrins tested. WO 97/19703 further reports that 2-hydroxypropylated β-cyclodextrin and maltosyl-β-cyclodextrin were not "feasible solubilizing agents for thyroxine, since they did not significantly improve the aqueous solubility of thyroxine even at higher applied concentrations."

There continues to be a need for liquid thyroid hormone formulations for oral administration that, for example, enable consistent dosing, are simple to administer, and/or remain stable. The following disclosure describes such formulations, as well as methods for making and using such formulations.

SUMMARY OF THE INVENTION

This invention provides liquid pharmaceutical compositions comprising a thyroid hormone solubilized in a pharmaceutically acceptable solvent. These compositions tend to be stable at typical storage temperatures, and are particularly useful for oral administration.

Briefly, therefore, this invention is directed, in part, to a liquid pharmaceutical composition comprising at least one thyroid hormone, hydroxypropyl-β-cyclodextrin ("HP-BCD"), and at least 5% (by weight) water. In generally preferred embodiments, the composition further comprises a buffer.

In some embodiments, the pH is at least about 8.

In some embodiments, the HPBCD concentration is at least 1% (by weight).

This invention also is directed, in part, to a method of using such a composition to treat a condition associated with impaired (i.e., deficient) thyroid hormone function in an animal.

This invention also is directed, in part, to use of such a composition to make a medicament for treating a disorder associated with impaired thyroid hormone function in an animal.

This invention also is directed, in part, to a process for making a pharmaceutical composition. In some such embodiments, for example, the process comprises combining levothyroxine sodium with an aqueous solution comprising a buffer and HPBCD. The composition comprises at least 5% (by weight) water.

Further benefits of Applicants' invention will be apparent to one skilled in the art from reading this specification.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

In accordance with this invention, Applicants surprisingly discovered that an aqueous liquid composition comprising HPBCD as a complexing agent can act, particularly in the presence of a buffer, as a solvent that is suitable for making a stable liquid thyroid hormone composition. Applicants have discovered such a solvent/buffer system is particularly suitable at a pH of at least 8. In some embodiments, for example, the pH is from 8 to about 12, or from about 10 to about 11. In other embodiments, the pH is at least about 9. In some such embodiments, for example, the pH is from about 9 to about 12, from about 9 to about 10.5, from about 10 to about 10.5, or from about 10.1 to about 10.3.

Thyroid hormones generally useful in the compositions of this invention comprise, for example, one or more of the following: levothyroxine; L-3,5,3'-triiodothyronine (also known as "liothyronine" or "LT3"); L-3,3',5'-triiodothyronine (also known as "LrT3"); L-3,5-diiodothyronine (also known as "LT2"); or mixtures thereof.

As used in this patent, the term "thyroid hormone" encompasses both a hormone itself, as well as any pharmaceutically acceptable salts (e.g., sodium salts) of the hormone. Thyroid hormones may exist as one or more polymorphic forms (for example one or more crystalline forms, amorphous forms, phases, solid solutions, and/or mixtures thereof), and the pharmaceutical compositions of this invention may be prepared from a pharmaceutically acceptable polymorphic form of a thyroid hormone and/or mixture thereof. Thyroid hormones also may exist in the form of solvates (e.g., hydrates), and the pharmaceutical compositions of this invention may be prepared from a solvate of the thyroid hormone and/or mixture thereof.

Thyroid hormones may be prepared synthetically as the biologically active l-enantiomer, or may be isolated directly from the thyroid gland of animals.

The concentration of thyroid hormone in the compositions of this invention will vary according to, for example, the unit dose or volume desired, and the particular thyroid hormone(s) that is used. Typically, the thyroid hormone concentration will be from about 0.1 mg/ml to about 2.0 mg/ml, particularly when the hormone comprises levothyroxine. In some embodiments, the concentration is about 1.0 mg/ml.

Cyclodextrins ("CDs") may be prepared from starches using CD-glucosyl transferase enzyme. There are three different kinds of CDs: α-, β- and γ-CD. These consist of 6, 7, or 8 glucopyranose units, respectively, connected with –1.4 glucosidic bonds. The three cyclodextrins differ in molecular weight, water-solubility, and cavity-diameter. These compounds are able to form inclusion complexes with other compounds. These inclusion complexes have different properties, depending on the CD. It should be noted that further modifications in the CD molecule also may be made with suitable substitutions. For example, in case of heptakis-2,6-di-0-methyl-β-CD ("DIMEB"), two hydroxy groups of every glucose unit are methylated, while in the case of randomly methylated β-CD ("RAMEB"), the hydroxy groups are substituted randomly by methoxy groups, which the average degree of methylation is around 1, 8. The hydroxyalkylation of cyclodextrins also results in improved aqueous solubility, as known for hydroxypropylated and hydroxyethylated cyclodextrin derivatives. Szejtli, *J Cyclodextrin Technology, p.* 51 (Kluwer Academic Publ., 1988).

A preferred hydroxyalkylated cyclodextrin is hydroxypropyl-β-cyclodextrin (or "HPBCD"), which generally is 2-hydroxypropyl-β-cyclodextrin. 2-Hydroxypropyl-β-cyclodextrin also is identified as "hydroxypropylbetadex" (European Pharmacopoeia name). It has the molecular formula $C_{42}H_{70}O_{35}(C_3H_6O)_x$, with x=7. Its European Pharmacopoeia monograph is 1804, and its CAS Number is 128446-35-5.

Preferably, the HPBCD concentration in the composition is greater than 1%. In some such embodiments, the HPBCD concentration is at least about 5% (by weight), or at least about 10% by weight. For example, in some embodiments, the HPBCD concentration is from about 10% to about 50% or from about 15% to about 30% (by weight). In some embodiments, the concentration is about 20% (by weight). Thus, in one embodiment, the composition comprises levothyroxine sodium, and from about 10% to about 50% (by weight) HPBCD. Such a composition preferably is in the form of an aqueous solution, with a pH of at least 8. In some embodiments, the pH is from 8 to about 12, or from about 10 to about 11. In other embodiments, the pH is at least about 9. In some such embodiments, for example, the pH is from about 9 to about 12, from about 9 to about 10.5, from about 10 to about 10.5, or from about 10.1 to about 10.3.

The amount of water in the composition will vary, depending on, for example, the desired total volume and the amount of thyroid hormone in the volume. Generally, the amount of water will be at least 5%, at least about 10%, at least about 25%, at least about 50%, or at least about 60% (by volume). In some embodiments, the amount of water will be no greater than about 80%, no greater than about 70%, or no greater than about 65% (by volume).

The composition typically further comprises at least one buffer. This buffer may serve multiple purposes.

For example, Applicants have observed that when levothyroxine sodium is combined with an aqueous HPBCD solution, the pH of the solution decreases. Due to this pH decrease, the pH must be monitored and base must be added to maintain the desired pH. Applicants have discovered that use of a buffer can reduce, or, more typically, entirely eliminate, the need for such monitoring and base addition. See, e.g., Example 7 below.

Applicants also have observed that, in the absence of a buffer, the pH of the composition tends to decrease over time while the composition is in partially-closed bulk storage containers, and also can decrease during long-term storage while the composition is in its final product packaging. These pH decreases, in turn, tend to reduce the stability of the composition. Applicants have discovered that the presence of a buffer can slow the rates of these pH decreases, thus increasing the stability of the composition over time. See, e.g., Examples 5, 8, and 9 below.

The buffer(s) preferably is effective (i.e., provides pH stability) at the preferred pH range, and typically has a pKa that falls within the preferred pH range. In general, the preferred pH of the compositions of this invention is at least about 8. In some embodiments, the preferred pH is from about 8 to about 12, or from about 10 to about 11. In other embodiments, the preferred pH is at least about 9. In some such embodiments, for example, the pH is from about 9 to about 12, from about 9 to about 10.5, from about 10 to about 10.5, or from about 10.1 to about 10.3. In other embodiments, the preferred pH is 9. In still other embodiments, the preferred pH is 10.2. Applicants have found that a pH within these ranges (and particularly a pH of 10.2) tends to be advantageous for dissolving levothyroxine sodium in an aqueous solution of 20% (w/v) HPBCD, and for extending the shelf-life of the finished product by preventing precipitation of the levothyroxine sodium over time.

In general, the buffer preferably has a pKa of at least about 9.5. In some embodiments, for example, the buffer has a pKa of from about 9.5 to about 10.7, from about 10 to about 10.7, or from about 10 to about 10.5.

In some embodiments, the buffer comprises sodium bicarbonate (also known as "sodium hydrogen carbonate"). Sodium bicarbonate is a commonly-used buffer for oral administration. When used as an excipient, sodium bicarbonate is regarded as an essentially nontoxic and nonirritant material. It is accepted for use as a food additive in Europe, and is listed in the FDA's Inactive Ingredients Guide and the FDA's Food Additive Database. In addition, sodium bicarbonate is known to be effective as a buffer over a pH range of 9.5 to 11.1. It also is known to have a $pKa_2$ of 10.3, which is close to the preferred pH of 10.2 for the composition. See, e.g., www.sigmaaldrich.com/Brands/Fluka_Riedel_Home/Bioscience/BioChemika_Ultra/Biological_Buffers.html (as published by Sigma-Aldrich Co. in 2006).

Examples of other contemplated buffers include those in Table 1:

TABLE 1

Examples of Other Contemplated Buffers

| Buffer | pKa* | effective pH range* |
|---|---|---|
| CABS (4-[cyclohexylamino]-1-butanesulfonic acid) | 10.70 | 10.0-11.4 |
| ethanolamine | 9.50 | 6.0-12.0 |
| AMP (2-amino-2-methyl-1-propanol) | 9.69 | 8.7-10.4 |
| Glycine | $pKa_2$ is 9.78 | 8.8-10.6 |
| CAPSO (3-[cyclohexylamino]-2-hydroxy-1-propanesulphonic acid) | 9.60 | 8.9-10.3 |
| Methylamine | 10.66 | 9.5-11.5 |
| CAPS (N-cyclohexyl-3-aminopropanesulfonic acid) | 10.40 | 9.7-11.1 |

*As reported in www.sigmaaldrich.com/Brands/Fluka__Riedel_Home/Bioscience/Bio-Chemika_Ultra/Biological_Buffers.html (as published by Sigma-Aldrich Co. in 2006).

The amount of buffer in the composition is preferably sufficient to impart the desired pH stability. The buffer (e.g., sodium bicarbonate) concentration is preferably at least about 0.001 mol/L, and typically at least about 0.005 mol/L. In some embodiments, the concentration is from about 0.005 to about 0.1 mol/L, or from about 0.01 to about 0.05 mol/L. For example, in some embodiments, the concentration is about 0.01 mol/L, about 0.02 mol/L, about 0.03 mol/L, or about 0.04 mol/L.

The composition may further comprise a pH-adjusting agent to obtain the desired pH. In some embodiments, for example, the pH-adjusting agent comprises NaOH. In other embodiments, the pH-adjusting agent may, for example, alternatively or additionally comprise a phosphate and/or carbonate.

It is contemplated that the solubility and stability of the thyroid hormone may, in some instances, be further improved by, for example, using various other solvents, surface modifiers, particle size reduction of the hormone (e.g., by micronisation), complexing agents, and the like.

For example, the composition may comprise from about 5% to about 30% (or from about 5% to about 20%) by weight of a pharmaceutically acceptable (and typically orally acceptable) preservative. The preservative preferably is compatible with the active ingredient(s), and has sufficient efficacy of antimicrobial preservation as outlined in European Pharmacopoeia 5.1.3 for oral preparations. In some embodiments, the preservative comprises ethanol. In some such embodiments, for example, the ethanol is present at a concentration of from about 5% to about 20%, or from about 10% to about 15% (v/v).

The composition may additionally comprise from a trace amount to about 5% or from about 1% to about 5% (by weight) of a pharmaceutically acceptable antioxidant. The presence of an antioxidant may aid in providing stability to the composition. Antioxidants that are often suitable for the compositions of this invention include, for example, ethylene diamine tetra-acetate salt ("EDTA"), sodium thiosulfate, sodium ascorbate, and/or propyl gallate. When EDTA is present, the preferred concentration is about 0.1%. When sodium thiosulfate is present, the preferred concentration is from a trace amount to about 0.5% (w/v), with about 0.025% (w/v) typically being preferred. When sodium ascorbate is present, the preferred concentration is from a trace amount to about 1% (w/v), with about 0.1% (w/v) typically being preferred. When propyl gallate is present, the preferred concentration is from a trace amount to about 1% (w/v), with about 0.1% (w/v) typically being preferred.

The composition may additionally comprise one or more other compounds that aid in the stability. It is contemplated that such compounds may include, for example, ammonium chloride and/or one or more iodide donors (e.g., sodium iodide). When sodium iodide is present, the preferred concentration is from a trace amount to about 0.5% (w/v).

Solubilization of the thyroid hormone may be achieved at lesser concentrations of HPBCD by adding a copolymer(s). Suitable copolymers may include, for example, sodium carboxymethyl cellulose ("CMC"), hydroxypropylmethylcellulose 4000 ("HPMC"), and/or povidone 12PF. When HPMC is present, the preferred concentration is from trace amount to about 1% (w/v), with about 1% (w/v) typically being preferred). When CMC is present, the preferred concentration is from a trace amount to about 1% (w/v), with about 1% (w/v) typically being preferred. When Povidone 12PF is present, the preferred concentration is from a trace amount to about 5% (w/v), with about 2% (w/v) typically being preferred.

The compositions of this invention may further comprise one or more physiologically acceptable formulation excipients, such as those described in "Gennaro, Remington: The Science and Practice of Pharmacy" (20th Edition, 2000) (incorporated by reference into this patent). The compositions may further comprise one or more other pharmaceutically acceptable ingredients, such as coloring agents, flavoring agents, thickening agents, for example povidone, carboxymethylcellulose, and/or hydroxypropyl methylcellulose. All such excipients and other ingredients preferably are (1) substantially pharmaceutically and/or veterinary pure and non-toxic in the amounts employed, and (2) compatible with the active ingredient(s). These excipients and other ingredients may be present in an amount of from a trace amount to about 40% (by weight). In some embodiments, the excipients and other ingredients are present in an amount of from a trace amount to about 10% (by weight).

The compositions of this invention are generally useful for treating conditions associated with impaired thyroid hormone function. The impaired thyroid activity may, for example, occur spontaneously or be the result of surgical removal of the thyroid gland, thyroiditis, or decreased function secondary to pituitary degeneration resulting in hypothyroidism. Whatever the cause of the hypothyroidism, it may be treated by hormone replacement therapy. Conditions secondary to the hypothyroidism may be treated with hormone replacement therapy as well. Those conditions include, for example, myxedema, cretinism, and/or obesity.

The compositions of this invention may be used with any species of animal in need of treatment for a condition associated with impaired thyroid hormone function. Such species may include, for example, birds, fish, reptiles, amphibians, and particularly mammals. Mammals include, for example, canines, such as, for example, dogs (including pure-bred and/or mongrel companion dogs, show dogs, working dogs, herding dogs, hunting dogs, guard dogs, police dogs, racing dogs, and/or laboratory dogs). Other mammals include felines, such as, for example, cats. Still other mammals include, for example, other companion animals (e.g., cats, rabbits, ferrets, etc.), farm or livestock mammals (e.g., swine, bovines, equines, goats, sheep, etc.), laboratory mammals (e.g., mice, rats, guinea pigs, etc.), and wild and zoo mammals (e.g., buffalo, deer, etc.).

The compositions of this invention are particularly suitable for oral administration. The term "oral formulation" means that the active ingredient(s) is formulated into a product suitable for administering to the animal via the mouth. These formulations may include, for example, liquids or semi-liquids, gels, pastes, oral sprays, buccal formulations, or animal feeds containing the active ingredients. Preferably, however, the composition is in the form of a liquid or semi-liquid solution, and typically an aqueous solution.

An oral formulation does not necessarily have to be administered to the animal independently of its food or water. Oral administration includes, for example, the administration of the composition in the animal's food or drinking water. In this instance, the composition may, for example, be dripped onto the food or drinking water. The composition also may, for example, be applied to the animal's coat such that the animal later ingests the composition during self-cleaning.

It is contemplated that compositions of this invention also may be administered parenterally, such as via subcutaneous injection, intravenous injection, intramuscular injection, intrasternal injection, submucosal injection, and infusion. It also is contemplated that compositions of this invention may be administered topically, such as via pour-on or spot-on.

In general, the composition is administered in a dosage that provides a therapeutically effective amount of the thyroid hormone to the recipient animal. This is particularly true where the hormone is the only active ingredient being administered to the animal. To the extent the hormone is administered with another active ingredient(s), the dosage preferably comprises an amount of the hormone that, together with the amount of other active ingredient(s), constitutes a therapeutically effective amount.

The term "therapeutically effective amount" means an amount sufficient to prevent, reduce the risk of, delay the onset of, ameliorate, suppress, or eradicate the condition being treated.

The preferred total daily dose of the thyroid hormone is typically from about 15 µg/Kg to about 25 µg/Kg body weight. In some embodiments, the preferred total daily dose of the hormone is about 20 µg/Kg body weight. Although single daily doses are typically preferred, it is contemplated that dosage unit compositions may contain less than the total daily dose, and that such smaller doses are administered two or more times per day to achieve the desired total daily dose. It should be recognized that multiple doses per day may, in some instances, be used to increase the total daily dose, if desired.

Factors affecting the preferred dosage regimen include the type (e.g., species and breed), age, weight, sex, diet, activity, condition, and past medical history of the animal patient; the severity of the pathological condition; the apparatus used to administer the composition (to the extent an apparatus is used); pharmacological considerations, such as the activity, efficacy, pharmacokinetic, and toxicology profiles of the particular composition administered; the existence of an additional active ingredient(s) in the composition; and whether the composition is being administered as part of a drug and/or vaccine combination. Thus, the dosage actually employed can vary for specific animal patients, and, therefore, can deviate from the typical dosages set forth above. Determining such dosage adjustments is generally within the skill of those in the art using conventional means. It is contemplated that the composition may be administered to the animal patient a single time. In general, however, the composition is administered daily over long periods, often the remainder of the animal's life.

The compositions of this invention may be used in adjunctive therapy with one or more other agents having activity in the treatment of conditions associated with impaired thyroid hormone function. Other agents may include, for example, thyreoglobulin.

A further aspect of the present invention is directed to the use of a thyroid hormone to prepare a pharmaceutical composition for treating a disorder associated with impaired thyroid hormone function in an animal (particularly a dog).

In some embodiments, for example, levothyroxine sodium is added to an aqueous solution that comprises HPBCD and a buffer. Typically, the pH of the aqueous solution is adjusted with base (e.g., NaOH) to obtain the desired pH (e.g., about 10.2) before the levothyroxine sodium is added. Other ingredients (e.g., ethanol) also may be added before the levothyroxine sodium is added. Such other ingredients, however, may alternatively (or additionally) be added at the same time as the levothyroxine sodium and/or after the levothyroxine sodium. Although typically less desirable, the buffer also may be added at the same time as the levothyroxine sodium and/or after the levothyroxine sodium rather than (or in addition to) being added before the levothyroxine sodium. In some preferred embodiments, the buffer is dissolved in water, followed by HPBCD addition and pH adjustment, before the levothyroxine sodium is added.

In other embodiments, a kneading process is used. To illustrate, a small amount of water is added to the HPBCD and levothyroxine sodium to form a paste that is then further diluted with water, ethanol, NaOH, and buffer.

EXAMPLES

The following examples are merely illustrative, and not limiting to the remainder of this disclosure in any way.

Example 1

Illustration of a Levothyroxine Sodium Composition

The following compositions were prepared:

| Ingredient | Amount |
| --- | --- |
| Levothyroxine sodium | 0.1% (w/v) |
| HPBCD | 20% (w/v) |
| Ethanol 96% (v/v) | 15% (v/v) |
| NaOH | to pH 10.2 ± 0.2 |
| Purified water | sufficient to bring the total volume of the composition to 100 ml |
| Levothyroxine sodium | 0.1% (w/v) |
| HPBCD | 30% (w/v) |
| Ethanol 96% (v/v) | 15% (v/v) |
| NaOH | to pH 10.2 ± 0.2 |
| Purified water | sufficient to bring the total volume of the composition to 100 ml |
| Levothyroxine sodium | 0.1% (w/v) |
| HPBCD | 20% (w/v) |
| Ethanol 96% (v/v) | 20% (v/v) |
| NaOH | to pH 10.2 ± 0.2 |
| Purified water | sufficient to bring the total volume of the composition to 100 ml |
| Levothyroxine sodium | 0.1% (w/v) |
| HPBCD | 30% (w/v) |
| Ethanol 96% (v/v) | 20% (v/v) |
| Methyl 4-hyrdoxybenzoate sodium salt | 0.2% (w/v) |
| EDTA tetrasodium salt | 0.1% (w/v) |
| NaOH | to pH 10.2 ± 0.2 |
| Purified water | sufficient to bring the total volume of the composition to 100 ml |
| Levothyroxine sodium | 0.1% (w/v) |
| HPBCD | 20% (w/v) |
| Ethanol 96% (v/v) | 10% (v/v) |
| NaOH | to pH 10.2 ± 0.2 |
| Purified water | sufficient to bring the total volume of the composition to 100 ml |
| Levothyroxine sodium | 0.1% (w/v) |
| HPBCD | 20% (w/v) |
| Ethanol 96% (v/v) | 15% (v/v) |
| Sodium bicarbonate | 0.084% (w/v) (0.01 mol/L) |
| NaOH | to pH 10.2 ± 0.2 |
| Purified water | sufficient to bring the total volume of the composition to 500 ml |
| Levothyroxine sodium | 0.1% (w/v) |
| HPBCD | 20% (w/v) |
| Ethanol 96% (v/v) | 15% (v/v) |
| Sodium bicarbonate | 0.168 (w/v) (0.02 mol/L) |
| NaOH | to pH 10.2 ± 0.2 |
| Purified water | sufficient to bring the total volume of the composition to 500 ml |
| Levothyroxine sodium | 0.1% (w/v) |
| HPBCD | 20% (w/v) |
| Ethanol 96% (v/v) | 15% (v/v) |
| Sodium bicarbonate | 0.336% (w/v) (0.04 mol/L) |
| NaOH | to pH 10.2 ± 0.2 |
| Purified water | sufficient to bring the total volume of the composition to 500 ml |
| Levothyroxine sodium | 0.1% (w/v) |
| HPBCD | 20% (w/v) |
| Ethanol 96% (v/v) | 15% (v/v) |
| Sodium bicarbonate | 0.84% (w/v) (0.1 mol/L) |
| NaOH | to pH 10.2 ± 0.2 |
| Purified water | sufficient to bring the total volume of the composition to 500 ml |

To prepare the above compositions that do not contain sodium bicarbonate, a small amount of water was added to the HPBCD to form a paste. Additional water and ethanol were then added, followed by NaOH while stirring to impart a pH of 10.2±0.2. Finally, the levothyroxine sodium (and, if applicable, the other components) was added while stirring the mixture.

For the compositions comprising sodium bicarbonate, the compositions were prepared by first introducing a large amount of water into the vessel to dissolve the sodium bicarbonate. The HPBCD was then introduced into the vessel, followed by ethanol. Afterward, NaOH was introduced to impart a pH of 10.2±0.2. Finally, the levothyroxine sodium was added while stirring the mixture.

Example 2

Effect of pH

Levothyroxine sodium is a tri-basic acid with three pKa's: 2.2, 6.7, and 10.1. Its solubility is affected by change of pH, and is lower at intermediate pH's (e.g., 28 μg/ml at pH 7.3). The solubility of levothyroxine sodium is 7 times greater at a pH of 9.4, and 11 times greater at a pH of 10.45 than at pH 7.3. To have an acceptable biological pH and to improve the solubility of levothyroxine, the pH preferably is at least about 8, or at least about 9.

Example 3

Effect of Levothyroxine Sodium Particle Size

The solubilities of batches of levothyroxine sodium micronized (D99<13 μm) and not micronized (D99<125 μm) were investigated. Preparations with several amounts of active ingredient in a fixed volume of water were observed after 24 hours. In both cases, less than 100 μg of levothyroxine sodium was soluble per ml of water. Thus, micronization alone did not improve the solubility or time of dissolution in water.

Example 4

Effect of Complexing Agent

In an aqueous solution of 30% (w/w) HPBCD (Kleptose HPB, Roquette, France), 1000 μg/ml of levothyroxine sodium was dissolved. Applicants have observed that similar levothyroxine sodium solubilities may be achieved at lesser concentrations of HPBCD by adding a copolymer(s), such as, for example, sodium carboxymethyl cellulose ("CMC"), hydroxypropylmethylcellulose 4000 ("HPMC"), and/or povidone 12PF. More specifically, Applicants observed that 1000 μg/ml of levothyroxine sodium was achieved in aqueous solutions having any of the following copolymer/HPBCD concentrations:
  0.5% w/w of CCM and 15% (w/w) of HPBCD,
  0.5% w/w of HPMC and 20% (w/w) of HPBCD, or
  2% w/w of Povidone 12PF and 20% (w/w) of HPBCD.

Example 5

Stability of First Formulation of Example 1 Above

The stability of levothyroxine in the first formulation of Example 1 was tested in 30 ml sealed type I glass bottles. After 6 months at 2-8° C., no significant changes were observed in appearance, levothyroxine content (+3.1%), liothyronine sodium, ethanol content, or pH. This is consistent with the results of a different experiment, wherein the levothyroxine content was observed to remain stable (−4.2%) over 9 months in a sealed 30 ml type I glass bottle at 2-8° C. After 6 months at 23-27° C. and 55-65% RH, a slight decrease of the levothyroxine content (−6.7%) and pH was observed. The preparations remained clear in all instances.

When 600 L of the first formulation of Example 1 was stored in a partially-closed container for 7 days at 2-8° C., the pH decreased by 1.6 units from 10.3 to 8.7.

Decreases in pH also were observed when the first formulation of Example 1 was stored in closed containers from 18 to 24 months. These decreases, however, were inconsistent, and ranged from little or no decrease to a decrease of up to 1.8 units.

Example 6

Stability Effects of Stabilizers on Levothyroxine Sodium Compositions

The stability of levothyroxine sodium in an aqueous solution of HPBCD with or without stabilization was investigated. The results are shown in Tables 2-4:

TABLE 2

Stability effects of CMC, HPMC, and Povidone 12PF

| Formulation | Storage condition | Remaining levothyroxine sodium |
|---|---|---|
| HPBCD 30% (w/w) in water | 2 month at 25° C. | 93% |
| | 2 month at 30° C. | 85% |
| | 2 month at 40° C. | 85% |
| HPBCD 30% (w/w) in water (vials filled under $N_2$) | 1 month at 25° C. | 95% |
| | 1 month at 30° C. | 90% |
| | 1 month at 40° C. | 85% |
| HPBCD 10% (w/w) in water, plus 2% (w/w) of povidone 12PF in water | 2 month at 25° C. | 91% |
| | 2 month at 30° C. | 87% |
| | 2 month at 40° C. | — |
| HPBCD 15% (w/w) in water, plus 0.5% (w/w) of CMC in water | 2 month at 25° C. | 97% |
| | 2 month at 30° C. | 92% |
| | 2 month at 40° C. | — |
| HPBCD 20% (w/w) in water, plus 0.5% (w/w) of HPMC in water | 2 month at 25° C. | 119%* |
| | 2 month at 30° C. | 108%* |
| | 2 month at 40° C. | NA |

*Preparations with HPMC are viscous, making sampling difficult. This explains the high values of levothyroxine sodium obtained with HPMC.

TABLE 3

Stability effects of antioxidants

| Formulation | Storage condition | Remaining levothyroxine sodium |
|---|---|---|
| HPBCD 30% (w/w) in water (reference) | 1 month at 25° C. | 92% |
| | 1 month at 40° C. | 84% |
| HPBCD 30% (w/w) in water in sodium thiosulfate (25 µg/ml) | 1 month at 25° C. | 100% |
| | 1 month at 40° C. | 97% |
| | 2 month at 25° C. | 104% |
| | 2 month at 30° C. | 110% |
| | 2 month at 40° C. | 82% |
| HPBCD 30% (w/w) in water, plus 0.1% (w/w) of sodium ascorbate in water* | 1 month at 25° C. | 92% |
| | 1 month at 40° C. | 92% |
| HPBCD 30% (w/w) in water, plus 0.1% (w/w) of sodium ascorbate in buffer phosphate* | 1 month at 25° C. | 88% |
| | 1 month at 40° C. | 79% |
| HPBCD 30% (w/w) in water, plus 0.1% (w/w) of propyl gallate in buffer phosphate* | 1 month at 25° C. | 70% |
| | 1 month at 40° C. | 71% |
| HPBCD 30% (w/w) in water, plus 0.1% (w/w) of EDTA di-sodium in water* | 1 month at 25° C. | 100% |
| | 1 month at 40° C. | 92% |

*Vials filled under $N_2$

TABLE 4

Stability effects of sodium iodide (an iodide donor), sodium thiosulfate (an antioxidant), and ammonium chloride

| Formulation | Storage condition | Remaining levothyroxine sodium |
|---|---|---|
| Water (reference) | 1 month at 40° C. | 87% |
| | 2 month at 40° C. | 78% |
| | 4.5 months at 25° C. | 83% |
| Sodium iodide 25 µg/ml | 1 month at 40° C. | 86% |
| | 2 month at 40° C. | 77% |
| | 4.5 months at 25° C. | 87% |
| Sodium iodide 125 µg/ml | 1 month at 40° C. | 86% |
| | 2 month at 40° C. | 73% |
| | 4.5 months at 25° C. | 88% |
| Sodium thiosulfate 25 µg/ml | 1 month at 40° C. | 96% |
| | 2 month at 40° C. | 89% |
| | 4.5 months at 25° C. | 95% |
| Sodium thiosulfate 250 µg/ml | 1 month at 40° C. | 106% |
| | 2 month at 40° C. | 105% |
| | 4.5 months at 25° C. | 85% |
| Ammonium chloride 5 µg/ml | 1 month at 40° C. | 86% |
| | 2 month at 40° C. | 85% |
| | 4.5 months at 25° C. | 82% |
| Sodium thiosulfate 25 µg/ml | 1 month at 40° C. | 74% |
| | 2 month at 40° C. | 75% |
| | 4.5 months at 25° C. | 85% |

In these experiments, the levothyroxine sodium did not exhibit incompatibility with HPBCD in aqueous solution.

Example 7

Use of a Buffer to Stabilize the pH of an HPBCD Solution During the Addition of Levothyroxine Sodium Applicants observed that just after levothyroxine sodium is added to an aqueous solution of 20% HPBCD at a pH of 10.2, the pH of the solution decreases by about 0.07 to 1.11 units. Applicants' observations are summarized below in Table 5:

TABLE 5 pH decrease after addition of levothyroxine sodium to an aqueous solution of HPBCD

| Experiment Number | 1 | 2 | 3 | 4 |
|---|---|---|---|---|
| Batch size | 30 L | 30 L | 500 ml | 500 ml |
| pH before introduction of levothyroxine sodium | 10.30 | 10.32 | 10.13 | 10.51 |
| pH at the end of introduction of levothyroxine sodium (before second pH adjustment) | 9.19 | 9.79 | 9.19 | 10.44 |
| Variation of pH | −1.11 | −0.53 | −0.94 | −0.07 |

Because of this pH decrease, an adjustment of pH was generally needed after the addition of the levothyroxine sodium to bring the pH back to the desired level. In accordance with this invention, Applicants included sodium bicarbonate in the aqueous HPBCD solution in an effort to reduce the decrease of the pH during the addition of the levothyroxine sodium, and, therefore, reduce or eliminate the need to measure and adjust the pH after the levothyroxine sodium is added. Applicants' observations are summarized below in Table 6 (laboratory scale) and Table 7 (pilot scale):

TABLE 6

Laboratory scale effects of sodium bicarbonate

| Experiment number | 1 | 2 | 3 | 4 |
|---|---|---|---|---|
| Batch size | 500 ml | 500 ml | 500 ml | 500 ml |
| Carbonate buffer content | 0.01 mol/L | 0.02 mol/L | 0.04 mol/L | 0.1 mol/L |
| pH before introduction of levothyroxine sodium | 10.23 | 10.36 | 10.36 | 10.16 |
| pH at the end of introduction of levothyroxine sodium | 10.21 | 10.34 | 10.31 | 10.13 |
| Variation of pH | −0.02 | −0.02 | −0.05 | −0.03 |

TABLE 7

Pilot scale effects of sodium bicarbonate

| | |
|---|---|
| Batch size | 30 L |
| Carbonate buffer content | 0.01 mol/L |
| pH before introduction of levothyroxine sodium | 10.42 |
| pH at the end of dissolution | 10.31 |
| Variation of pH | −0.11 |

The sodium bicarbonate had no influence on the time of dissolution of the levothyroxine sodium in any of these laboratory-scale and pilot-scale experiments.

Example 8

Assessment of the Buffering Capacity of Sodium Bicarbonate

Applicants assessed the buffering capacity of sodium bicarbonate in a final product containing 0.1% (w/v) levothyroxine sodium dissolved in an aqueous 20% (w/v) HPBCD solution by evaluating the amount of a 0.5% (v/v) HCl solution required to decrease the pH by 0.1 and 1.0. Applicants' observations are summarized below in Table 8:

TABLE 8

Quantity of 0.5% HCl required to move pH by 0.1 and 1 unit

| Quantity of 0.5% HCl required to decrease the pH by: | Expt. 1 No sodium bicarbonate | Expt. 2 0.01 mol/L sodium bicarbonate | Expt. 3 0.02 mol/L sodium bicarbonate | Expt. 4 0.04 mol/L sodium bicarbonate |
|---|---|---|---|---|
| 0.1 | 0.0610 g | 0.0270 g | 0.2181 g | 0.3562 g |
| 1.0 | 0.2726 g | 0.7806 g | 1.3829 g | NA |

Example 9

Stability of Levothyroxine Sodium Compositions with a Buffer

Applicants investigated the stability of levothyroxine sodium in aqueous HPBCD solutions with phosphate and carbonate buffers in a sealed container. The results are summarized below in Table 9:

TABLE 9

Stability effects of phosphate and carbonate buffers

| Formulation | Storage condition | Remaining levothyroxine sodium |
|---|---|---|
| HPBCD 30% (w/w) in water | 2 month at 25° C. | 93% |
| | 2 month at 30° C. | 85% |
| | 2 month at 40° C. | 85% |
| HPBCD 30% (w/w) in a di-sodium phosphate buffered solution at a pH of 10 | 2 month at 25° C. | 99% |
| | 2 month at 30° C. | 92% |
| | 2 month at 40° C. | 73% |
| HPBCD 30% (w/w) in a sodium carbonate buffered solution at a pH of 10 | 2 month at 25° C. | 100% |
| | 2 month at 30° C. | 98% |
| | 2 month at 40° C. | 91% |

In these experiments, the levothyroxine sodium did not exhibit incompatibility with HPBCD in aqueous solution.

Applicants also investigated the stability of levothyroxine sodium in an aqueous HPBCD solution with sodium bicarbonate after being stored in an open container at 2-8° C. or 30° C. Closed bottles stored in the same conditions were used as references. The results are summarized below in Table 10:

TABLE 10

Stability of buffered composition in open containers

| Experiment number | 1 | 2 | 3 | 4 | 5 |
|---|---|---|---|---|---|
| Batch size | 30 L | 500 ml | 500 ml | 500 mL | 500 ml |
| Storage condition | 2-8° C. | 2-8° C. | 2-8° C. | 30° C. | 30° C. |
| Storage duration (days) | 34 | 20 | 20 | 2 | 2 |
| Carbonate buffer content (mol/L) | 0.01 | 0.02 | 0.04 | 0.01 | 0.04 |
| pH opened bottle | 9.28 | 9.58 | 9.86 | 9.6 | 9.9 |
| pH closed bottle | 10.31 | 10.36 | 10.61 | 10.3 | 10.3 |
| Difference | −1.03 | −0.78 | −0.75 | −0.7 | −0.4 |

The words "comprise," "comprises," and "comprising" in this patent (including the claims) are to be interpreted inclusively rather than exclusively. This interpretation is intended to be the same as the interpretation that these words are given under United States patent law.

When a concentration percentage is characterized "by volume," the percentage is the volume of the described ingredient per total volume of the composition. When a concentration percentage is characterized "by weight," the percentage is the weight of the described ingredient per total weight of the composition.

Unless otherwise indicated, a "trace amount" is an amount that is detectable, but too small to be quantified.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:
1. A pharmaceutical composition comprising:
   from 0.1 mg/ml to 0.2 mg/ml levothyroxine or a pharmaceutically acceptable salt thereof,
   from about 10% to about 50% (by weight) hydroxypropyl-β-cyclodextrin,
   at least one buffer having a pKa of at least about 9.5,
   at least 5% (by weight) water,
   a preservative at a concentration of no greater than about 30% (by weight),
   from about 5% to about 20% (by weight) ethanol, and
   a pharmaceutically acceptable antioxidant at a concentration of no greater than about 5% (by weight);
   wherein the pharmaceutical composition is liquid and has a pH of from about 10 to about 10.5.
2. The pharmaceutical composition of claim 1, wherein the pH of the composition is from about 10.1 to about 10.3.
3. The pharmaceutical composition of claim 1, wherein the composition further comprises NaOH.
4. The pharmaceutical composition of claim 1, wherein the buffer comprises sodium bicarbonate.
5. A method of treating a disorder associated with impaired thyroid hormone function in an animal, wherein the method comprises administering a therapeutically effective amount of a pharmaceutical composition of claim 1 to the animal.
6. The method of claim 5, wherein the animal is a dog.
7. The method of claim 5, wherein the condition comprises hypothyroidism.

* * * * *